(12) United States Patent
Smith et al.

(10) Patent No.: US 6,577,128 B1
(45) Date of Patent: Jun. 10, 2003

(54) NQR METHOD AND APPARATUS FOR TESTING A SAMPLE BY APPLYING MULTIPLE EXCITATION BLOCKS WITH DIFFERENT DELAY TIMES

(75) Inventors: John Alec Sydney Smith, London (GB); James Barras, London (GB); Neil Francis Peirson, Northampton (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/985,695

(22) Filed: Nov. 5, 2001

Related U.S. Application Data

(63) Continuation of application No. 09/549,722, filed on Apr. 14, 2000, now abandoned, which is a continuation of application No. PCT/GB98/03099, filed on Oct. 15, 1998.

(51) Int. Cl.[7] .................................................. G01V 3/00
(52) U.S. Cl. ....................................................... 324/309
(58) Field of Search .................................. 324/309, 307

(56) References Cited

U.S. PATENT DOCUMENTS

| | | | | |
|---|---|---|---|---|
| 4,887,034 A | * | 12/1989 | Smith | 324/307 |
| 5,365,171 A | | 11/1994 | Buess et al. | |
| 5,500,591 A | * | 3/1996 | Smith et al. | 324/300 |
| 5,583,437 A | * | 12/1996 | Smith et al. | 324/307 |
| 6,091,240 A | * | 7/2000 | Smith et al. | 324/300 |
| 6,127,824 A | * | 10/2000 | Smith et al. | 324/300 |
| 6,166,541 A | * | 12/2000 | Smith et al. | 324/300 |
| 6,208,136 B1 | * | 3/2001 | Smith et al. | 324/300 |
| 6,222,364 B1 | * | 4/2001 | Smith et al. | 324/300 |
| 6,246,237 B1 | * | 6/2001 | Smith et al. | 324/307 |

FOREIGN PATENT DOCUMENTS

| | | |
|---|---|---|
| WO | WO94/12891 | 6/1994 |
| WO | 96/26453 | 8/1996 |

OTHER PUBLICATIONS

Buess, et al; "NQR Detection Using a Meanderline Surface Coil", Journal of Magnetic Resonance; 92(1991) Apr., No. 2, pp. 348–362.

* cited by examiner

*Primary Examiner*—Edward Lefkowitz
*Assistant Examiner*—Dixomara Vargas
(74) *Attorney, Agent, or Firm*—Nixon & Vanderhye

(57) ABSTRACT

Methods of and apparatus for Nuclear Quadrupole Resonance (NQR) testing a sample containing quadrupolar nuclei exhibiting a given value of spin-lattice relaxation time, $T_1$, are disclosed. The method comprises applying two excitation blocks to excite nuclear quadrupole resonance, there being a given delay time between the two blocks, detecting resonance response signals, and comparing the response signals from respective blocks. The delay time is less than the $T_1$ value of the nuclei.

33 Claims, 12 Drawing Sheets

NQR METHOD AND APPARATUS FOR TESTING A SAMPLE BY APPLYING MULTIPLE EXCITATION BLOCKS WITH DIFFERENT DELAY TIMES

This application is a continuation of Ser. No. 09/549,722, filed Apr. 14, 2000, abandoned, which is a continuation of PCT/GB98/03099, filed Oct. 15, 1998, which claims priority from British Priority Patent Application No. 9721892.9, filed Oct. 15, 1997.

The present invention relates to methods of and apparatus for Nuclear Quadrupole Resonance (NQR) testing a sample. The invention has particular application to the detection of the presence of a given substance in a sample. The sample may contain or be suspected of containing nuclei of integral or half-integral spin quantum number ($I \geq \frac{1}{2}$). The invention is particularly suited to the testing of substances displaying weak NQR signals, and/or having low NQR frequencies, or more especially having long values of spin-lattice relaxation time ($T_1$), in circumstances where interfering signals (as later discussed) may be encountered.

BACKGROUND OF THE INVENTION

Substances which have relatively low NQR frequencies (perhaps 1 or 2 MHz or less) and relatively long values of $T_1$ (perhaps 500 ms, 5 or 10 s or more) include the explosives PETN and TNT, Potassium Nitrate ($KNO_3$) and $^{27}Al$ in alumina. For example, PETN has resonance frequencies around 0.9 MHZ, a $T_1$ of roughly 30 s at room temperature, as well as a spin-spin relaxation time ($T_2$) of approximately 20 ms. It is noted in passing that $T_2$ is preferably defined herein as the exponential constant measured by means of a Hahn echo or similar pulse sequence.

NQR testing is used for detecting the presence or disposition of specific substances, and in particular polycrystalline substances. It depends on the energy levels of quadrupolar nuclei, which have a spin quantum number I greater than ½, of which $^{14}N$ is an example (I=1). $^{14}N$ nuclei are present in a wide range of substances, including animal tissue, bone, food stuffs, explosives and drugs. One particular use of the technique described herein is in the detection of the presence of substances such as explosives or narcotics. The detection may be of baggage at airports, or of explosives or drugs concealed on the person or buried underground or elsewhere. Other nuclei of interest are $^{27}Al(I=5/2)$ and $^{63}Cu(I=3/2)$. $^{27}Al$ is present in minerals, cement and concrete, whilst $^{63}Cu$ is present in ores and many high Tc superconducting materials.

In conventional Nuclear Quadrupole Resonance testing a sample is placed within or near to a radio-frequency (rf) coil and is irradiated with pulses or sequences of pulses of electro-magnetic radiation having a frequency which is at or very close to a resonance frequency of the quadrupolar nuclei in a substance which is to be detected. If the substance is present, the irradiant energy will generate a precessing magnetization which can induce voltage signals in a coil surrounding the sample at the resonance frequency or frequencies and which can hence be detected as a free induction decay (f.i.d.) during a decay period after each pulse or as an echo after two or more pulses. These signals decay at a rate which depends on the time constants $T_2^*$ for the f.i.d., $T_2$ and $T_{2e}$ for the echo amplitude as a function of pulse separation, and $T_1$ for the recovery of the original signal after the conclusion of the pulse or pulse sequence.

As described in International Patent Application No. WO 96/26453 in the name of British Technology Group Limited, the subject matter of which is incorporated herein by reference, spurious interfering signals (also termed "ringing") which are not associated directly with or due to the nuclear resonance may sometimes arise from a sample during NQR tests.

For example, one group of materials which can cause interference problems includes metallic conductors. Such materials may be commonly found in many types of objects in baggage. It has been discovered that the interference may be particularly pronounced when a sample includes metallic or ferromagnetic material as a layer of plating on another material, especially, it has been found, when the plating layer comprises Nickel. Objects which are particularly prone to such problems include screws or key-rings. The cause of this type of interference has not been proven, but it is believed to emanate from ferromagnetic or like resonance effects in the $B_1$ field of the sample coil, and be due to a form of magneto-acoustic ringing. It should be emphasised that this interference is not an artefact of the particular detection apparatus used, but a feature of the material itself. Also it will be understood that, in the context of the detection of the presence of a particular substance in a sample, it would usually not be the particular nuclear species to be detected but the remainder of the sample which would give rise to the interfering signals.

The spurious interfering signals (or "artefacts") commonly have decay characteristics very similar to those of true NQR signals, and, furthermore, are often many times stronger; they can last for several milliseconds. The phase of those interfering signals and that of the resonance response signal following a single radio-frequency excitation pulse are entirely determined by the rf phase within the pulse. There is, however, one important distinction. When two or more pulses are used, the phase of the NQR response signal, whether it be a free induction decay (f.i.d.) or an echo, depends on the relative phases of the two preceding pulses, unlike that of the interfering signal, which is determined almost entirely by that of the immediately preceding pulse.

This distinction has been exploited in WO 96/26453 in an attempt to remove the interfering signal from an NQR response signal. The proposed solution involves the use of at least one pair of excitation pulse sequences (or blocks) in which the phase of the pulses is controlled in such a way that when the response signals from the two member sequences of the pair are compared the spurious signals can be largely eliminated whilst the genuine NQR signals can be retained.

SUMMARY OF THE INVENTION

It has been discovered pursuant to the present invention that, when applying a multiple pulse sequence such as one of those described in WO 96/26453, the response off-resonance varies with frequency in a periodic fashion. An example of a typical off-resonance response to a multiple pulse sequence for a typical substance is shown in FIG. 1. The response has been found to have narrow peaks and wide troughs which are believed to be due to the pulsed nature of the excitation; the separation of the peaks is believed to be related to the pulse repetition rate. Furthermore, the resonance frequency of the peaks varies with temperature and other such environmental parameters. Unless the excitation is exactly at the resonance frequency, or exactly at the frequency of one of the other peaks, there will not reliably be any response signal. Therefore, for example, in a typical situation (such as airport security checking) where the exact temperature of the sample is not known, the usefulness of such multiple pulse sequences may be reduced.

Further, it has been found pursuant to the present invention that the off-resonance behaviour of multiple pulse sequences can cause particular problems when they are used in pairs as described above to reduce spurious signals, particularly if the substance under test has a relatively low resonance frequency and/or long spin-lattice relaxation time.

The present invention seeks to maintain or improve upon the level of spurious signal suppression achieved using the technique described in WO 96/26453, but to improve the off-resonance response, especially for long $T_1$ substances. The invention also seeks to improve the sensitivity of NQR tests. The invention is based in part upon the discovery, pursuant to the invention, that an improvement in the off-resonance response and the sensitivity of the NQR test may result if the delay time between the two excitation pulse blocks mentioned above is carefully controlled.

Prior to the present invention, it was considered that sufficient time must be left between the two excitation blocks to allow the NQR magnetization generated during the first block to recover. However, it has now been discovered pursuant to the present invention that, by having a delay between the two blocks which is insufficient for the magnetization to recover, the off-resonant response behaviour and the sensitivity of the NQR test may be considerably improved.

According to the present invention there is provided a method of Nuclear Quadrupole Resonance testing a sample containing quadrupolar nuclei exhibiting a given value of spin-lattice relaxation time, $T_1$, the method comprising:

applying two (or possibly more) excitation blocks to excite nuclear quadrupole resonance, there being a given delay time between the two blocks;

detecting resonance response signals; and comparing the response signals from respective blocks;

wherein the delay time is less than the $T_1$ value of the nuclei.

By having a delay between the two blocks which is less than the $T_1$ value of the nuclei (that is, a delay which gives insufficient time for the magnetization to recover), the off-resonant response behaviour and the sensitivity of the NQR test may be considerably improved. This may allow improved detection of substances displaying weak NQR signals, in situations where the exact temperature of the sample is not known.

Each excitation block (or sub-block) may comprise one or more excitation pulses which generates an NQR response. Preferably, each excitation block comprises at least two, three, five or ten pulses, although it may comprise a multiplicity of pulses, say more than one hundred or even more than one thousand pulses. Suitably, the separation between each pulse may be less than, preferably less than one tenth of, the ring-down time (decay time) of the spurious interfering signals. Preferably, the separation between the pulses in a block is the same. Preferably the separation between the pulses is as defined in WO 96/26453 in relation to the SSFP and PSL pulse sequences. For example, the separation may be less than ten times, or five times, or three times or twice the value of the free induction decay time $T_2^*$. Indeed, the separation may be less than $T_2^*$ or a half $T_2^*$.

Preferably (in any embodiment whatsoever), where there are a plurality of pulses in each block (or sub-block), there is no phase alternation between those pulses. As used herein, the term "phase alternation" connotes a variation of phase of more than 90°, preferably more than 135°, and more preferably of roughly 180°. Accordingly, "no phase alternation" implies a variation of phase certainly less than 180°, preferably less than or equal to 135°, and more preferably less than or equal to 90°.

Preferably, the comparison takes the form of a combination of the responses from the respective blocks such that the NQR signal is enhanced while any spurious signals are reduced. In one embodiment, the comparison takes the form of a subtraction of the responses from the respective blocks, possibly with some weighting being given to one of the blocks to account for differences in the signal levels generated by the blocks. In other embodiments involving blocks having two or more constituent sub-blocks, the responses from the sub-blocks of one block are combined with the responses from either corresponding, or indeed non-corresponding, sub-blocks of the other block, such that the overall NQR signal is enhanced.

Advantageously, the delay time is less than half, preferably less than a quarter, more preferably less than a tenth and even more preferably less than a hundredth of the $T_1$ value. In short, it is preferable that the delay time is very much less than the spin-lattice relaxation time of the nuclei.

It is also preferred that the delay time is greater than the spin-spin relaxation time, $T_2$, of the nuclei, and hence advantageously the delay time is greater than once, preferably greater than twice, more preferably greater three times and even more preferably greater than five times the $T_2$ value. This can ensure effective relaxation of the magnetization in the x-y plane.

On the other hand, preferably, the delay time is less than ten times and more preferably less than five times the $T_2$ value, since this can maintain the duration of the test within a reasonable limit.

For typical nuclei of interest, preferred ranges of the delay time are between 1 and 1000 ms, preferably between 5 and 500 ms, more preferably between 10 and 100 ms and even more preferably between 20 and 60 ms.

One important feature of the present invention alluded to above is the discovery pursuant to the invention of the nature of the off-resonance performance in NQR of multiple pulse sequences. In order to improve the performance, preferably the first and second blocks, and the delay time therebetween, are arranged such that, if the resonance frequency of the nuclei were varied over a given range, the first and second blocks would generate response signals whose variation with frequency over the given range would in combination be less than for the response signals from separately either the first or second block. By arranging the first and second blocks and the delay time therebetween thus, the periodic variation of the response signals with frequency can be to an extent mitigated. It is in particular preferred if the peaks in the frequency response characteristic of one excitation block are arranged to coincide generally with the troughs in the characteristic of the other block, and vice versa.

It has been discovered pursuant to the present invention that the off-resonance response and the sensitivity of the NQR test may be further improved by applying excitation between the two excitation blocks. Therefore the method may further comprise applying excitation between the two excitation blocks. Preferably, the excitation is in the form of one or more excitation pulses, such pulses being termed herein "bridging pulses". By the use of such excitation the behaviour of the second block can be adjusted so that the overall pulse sequence can produce the desired improved result. In particular, the excitation between the two blocks can be used to improve the combined off-resonance behaviour of the two blocks.

In one preferred embodiment, an excitation pulse (herein termed "refocussing pulse") is applied, at a time substantially coincident with the last echo generated by the first block.

In another preferred embodiment an excitation pulse (herein termed "windmill pulse") is applied at a time adjacent the centre of the delay time between the two blocks.

In another preferred embodiment, excitation pulses are applied between the excitation blocks to provide saturation. Such pulses may be termed "saturation pulses".

Various preferred features of the excitation applied between the two blocks are as follows.

If one (or more) excitation pulse is applied between the two blocks, the (or each) pulse may have an effective flip angle of between 20° and 160°, or 200° and 340°, or 30° and 60°, or 70° and 110°, or 160° and 200°. It is noted in passing that the term "effective" in relation to a 90° flip angle is used to connote the NQR equivalent of a Nuclear Magnetic Resonance (NMR) 90° flip angle; in fact all flip angles referred to herein are "effective" flip angles.

If a plurality of excitation pulses is applied between the blocks, the second such pulse may be of the same or different flip angle as the first.

Each excitation block may comprise a first excitation sub-block and a second excitation sub-block, the response to one of the first and second sub-blocks in one block being compared to the response to one of the first and second sub-blocks in the other block. This can afford the advantage that by dividing the blocks into sub-blocks the off-resonance performance of the entire sequence can be enhanced, especially if the sub-blocks in each main block are different. Preferably, the response to the other of the first and second sub-blocks in one block is compared to the response to the other of the first and second sub-blocks in the other block as well.

This important feature is provided independently. Accordingly, the invention provides a method of Nuclear Quadrupole Resonance testing a sample containing quadrupolar nuclei exhibiting a given value of spin-lattice relaxation time, $T_1$, the method comprising applying two excitation blocks to excite nuclear quadrupole resonance, each excitation block comprising a first excitation sub-block and a second excitation sub-block, there being a given delay time between the two blocks, detecting resonance response signals, and comparing the response to one of the first and second sub-blocks in one block and the response to one of the first and second sub-blocks in the other block, the delay time being less than five times the $T_1$ value of the nuclei (that is, a delay which gives insufficient time for the magnetization to recover).

Preferably, the delay time is less than three times or twice the $T_1$ value of the nuclei; and more preferably the delay time is less than the $T_1$ value itself. Advantageously, the delay time is less than half, preferably less than a quarter, more preferably less than a tenth and even more preferably less than a hundredth of the $T_1$ value.

The first sub-block in each excitation block may be different from the second sub-block in each excitation block. For example, each sub-block may comprise a plurality of pulses, and the repetition rate of the pulses in the first sub-block may be different from the repetition rate of the pulses in the second sub-block. This can make the off-resonance response different between the first and the second sub-blocks, so that the combined off-resonance response can be improved.

If each excitation block comprises a plurality of excitation pulses, preferably the time between the first and second such pulse in the first block is different from the corresponding time for the second block. This has been found to be a particularly effective way of improving the off-resonance performance of the combined response signal from the first and second blocks.

For efficiency and optimum reduction in spurious signals, preferably each excitation block comprises a multiplicity of excitation pulses and at least the majority of the pulses in one block are substantially the same as the corresponding pulses in the other block.

One multiple pulse sequence of particular efficiency has been found to be a Pulsed Spin Locking (PSL) type sequence. In putting such a sequence into practice with the present invention, preferably each block comprises an initial preparation pulse followed by at least one pulse of different phase from the preparation pulse.

The feature that the time between the first and second such pulse in the first block is different from the corresponding time for the second block can be used particularly effectively in the context of a PSL type sequence. Accordingly, preferably, for one of the blocks the time between the preparation pulse and the immediately following pulse is half the time between subsequent pulses in the block, whereas preferably for (the other) one of the blocks the time between the preparation pulse and the immediately following pulse is substantially the same as the time between subsequent pulses in the block.

Another particularly effective pulse sequence in the context of the present invention is a Steady State Free Precession (SSFP) type sequence. In putting this sequence into practice for the present invention, preferably each excitation block comprises a plurality of excitation pulses, the time between each such pulse being the same.

In fact, repeated use of an SSFP type pulse sequence in a $T_1$ limited fashion has been found—surprisingly—to afford a number of benefits in reducing spurious interfering signals. Accordingly, the present invention provides a method of Nuclear Quadrupole Resonance testing a sample containing quadrupolar nuclei exhibiting a given value of spin-lattice relaxation time, $T_1$, the method comprising:

applying two (or more) excitation blocks to excite nuclear quadrupole resonance, there being a given delay time between the two blocks, each excitation block comprising a plurality of excitation pulses, the time between each such pulse being the same; and detecting resonance response signals;

wherein the delay time is less than five times the $T_1$ value of the nuclei.

Preferably, the delay time is less than three times or twice the $T_1$ value of the nuclei; and more preferably the delay time is less than the $T_1$ value itself. Advantageously, the delay time is less than half, preferably less than a quarter, more preferably less than a tenth and even more preferably less than a hundredth of the $T_1$ value.

The method may further comprise comparing the response signals from the respective blocks.

One particular preferred embodiment has been found to be where the phase of each pulse is the same. Also, if a plurality of pulses is provided in each block (or sub-block), preferably each (or most) of the pulses in that block (or sub-block) has the same or nearly the same phase; this may exclude the initial pulse in each block, which may be of a different phase. Preferably each (or most) of the pulses in that block (or sub-block) have phases which are within 90° of each other.

Each excitation block may comprise at least one excitation pulse, and at least one of the pulses may be a phase split pulse.

Although reference has been made above largely to the use of two excitation blocks, one or more further pairs of blocks with the appropriate delay (for example, less than the $T_1$ value of the nuclei, as taught previously) between each block of the pair could be used. Each pair of blocks may have substantially the same delay between the blocks, or the delays may be different. Each pair may be applied at a (slightly) different excitation frequency, in order to improve off-resonance performance.

The invention also provides apparatus for Nuclear Quadrupole Resonance testing a sample containing quadrupolar nuclei, comprising:

means (such as an rf probe) for applying two (or more) excitation blocks to excite nuclear quadrupole resonance, there being a given delay time between the two blocks:

means (such as the or another rf probe) for detecting resonance response signals from the blocks; and means (such as a processor) for comparing the response signals from the respective blocks;

wherein the delay time is between 1 and 1000 ms, preferably between 5 and 500 ms, more preferably between 10 and 100 ms and even more preferably between 20 and 60 ms.

Preferably, the first and second blocks, and the delay time therebetween, are arranged such that if the resonance frequency of the nuclei were varied over a given range, the first and second blocks would generate response signals whose variation with frequency over the given range would in combination be less than for the response signals from separately either the first or second block.

Preferably, the excitation applying means is adapted to apply excitation between the two excitation blocks. The excitation applying means may be adapted to apply an excitation pulse at a time substantially coincident with the last echo generated by the first block. The excitation applying means may be adapted to apply an excitation pulse at a time adjacent the centre of the delay time between the two blocks. The excitation applying means may be adapted to apply an excitation pulse between the two blocks and the pulse may have an effective flip angle of between 20° and 160°, or 200° and 340°, or 30° and 60°, or 70° and 110°, or 160° and 200°. The excitation applying means may be adapted to apply a plurality of excitation pulses between the two blocks, the second such pulse being of the same or different flip angle as the first.

Each excitation block may comprise a first excitation sub-block and a second-excitation sub-block, and the comparing means may be adapted to compare the response to one of the first and second sub-blocks in one block and the response to one of the first and second sub-blocks in the other block.

In a closely related apparatus aspect of the present invention there is provided apparatus for Nuclear Quadrupole Resonance testing a sample containing quadrupolar nuclei exhibiting a given value of spin-lattice relaxation time, $T_1$, comprising means for applying two excitation blocks to excite nuclear quadrupole resonance, each excitation block comprising a first excitation sub-block and a second excitation sub-block, there being a given delay time between the two blocks, means for detecting resonance response signals, and means for comparing the response to one of the first and second sub-blocks in one block and the response to one of the first and second sub-blocks in the other block, the delay time being less than five times $T_1$, for example, between 1 and 1000 ms, preferably between 5 and 500 ms, more preferably between 10 and 100 ms and even more preferably between 20 and 60 ms.

The first sub-block in each excitation block may be different from the second sub-block in each excitation block. For example, each sub-block may comprise a plurality of pulses, and the repetition rate of the pulses in the first sub-block may be different from the repetition rate of the pulses in the second sub-block.

The present invention also provides apparatus for Nuclear Quadrupole Resonance testing a sample containing quadrupolar nuclei, comprising:

means for applying two (or more) excitation blocks to excite nuclear quadrupole resonance, there being a given delay time between the two blocks, each excitation block comprising a plurality of excitation pulses, the time between each such pulse being the same; and means for detecting resonance response signals;

the delay time being less than five times $T_1$, for example, between 1 and 1000 ms, preferably between 5 and 500 ms, more preferably between 10 and 100 ms and even more preferably between 20 and 60 ms.

One particular preferred embodiment has been found to be where the phase of each pulse is the same.

Preferably, means for comparing the response signals from the respective blocks are provided.

Method and apparatus features of the invention may where appropriate be interchanged.

BRIEF DESCRIPTION OF THE DRAWINGS

Preferred features of the present invention will now be described, purely by way of example, with reference to the accompanying drawings, in which.

PREFERRED EMBODIMENT OF APPARATUS

Figure 2:
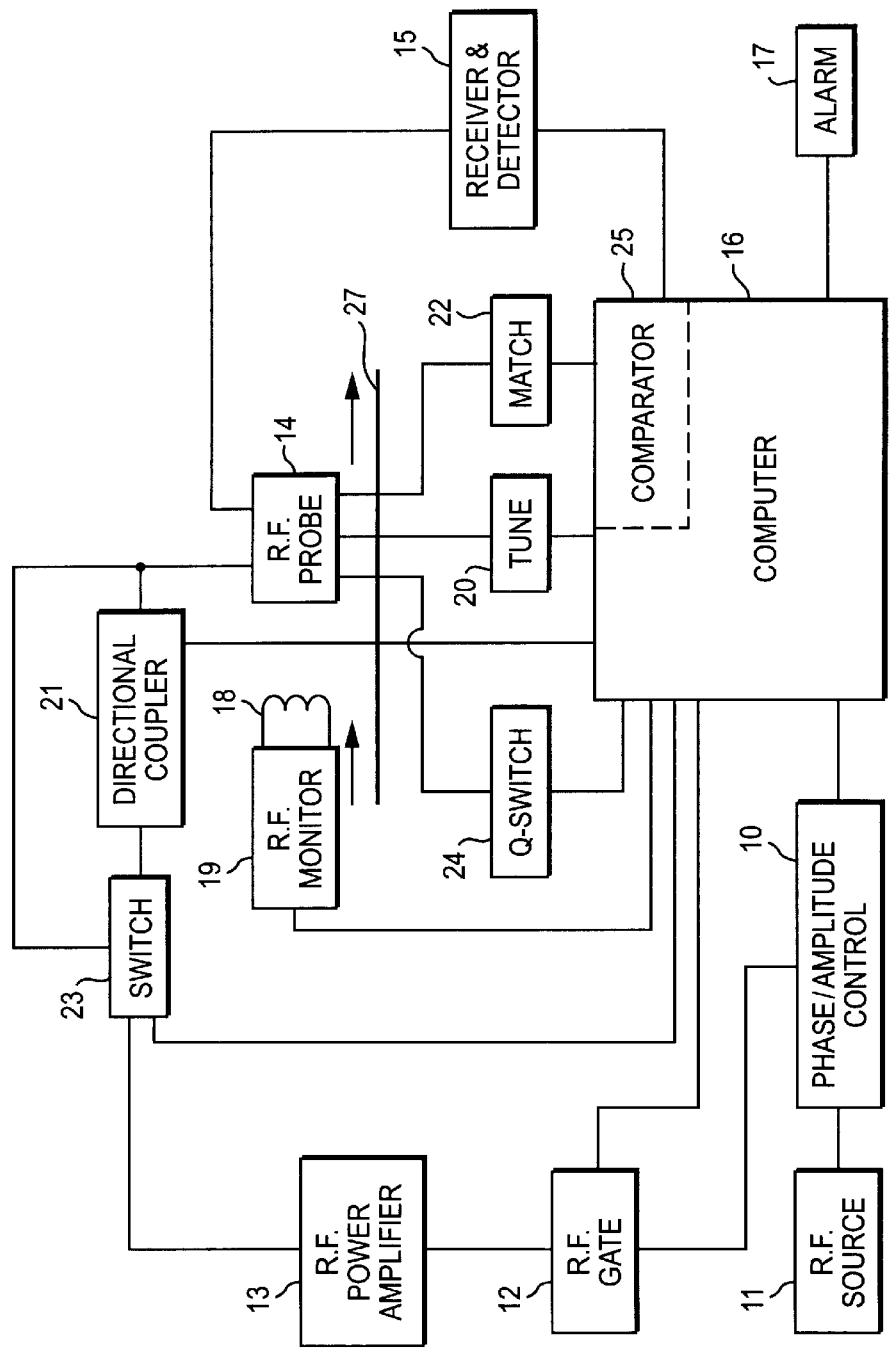
FIG. 2 shows a block diagram of a preferred embodiment of NQR apparatus.

Referring first to FIG. 2, a preferred embodiment of apparatus for NQR testing includes a radio-frequency source 11 connected via a phase/amplitude control 10 and a gate 12 to an rf power amplifier 13. The output of the latter is connected to an rf probe 14 which contains one or more rf coils disposed about or adjacent to the sample to be tested (not shown), such that the sample can be irradiated with rf pulses at the appropriate frequency or frequencies to excite nuclear quadrupole resonance in the substance under test (for example, an explosive). The rf probe 14 is also connected to rf receiver and detection circuitry 15 for detecting nuclear quadrupole response signals. The detected signal is sent from circuitry 15 to a control computer 16 (or other control apparatus) for processing, and for signal addition or subtraction. The computer includes some means 17 for producing an alarm signal in dependence upon whether a given threshold of detection for the presence of the particular substance of interest has been exceeded. The alarm signal would normally be used to activate an audio or visual alarm to alert the operator to the presence of the substance under test.

The control computer 16 also controls all pulses, their radio frequency, time, length, amplitude and phase. In the context of the present invention all of these parameters may need to be adjusted precisely; for example, phase may need to be varied in order to be able to generate echo responses.

Re-tuning of the rf probe 14, alteration of its matching and alteration of its Q factor may all need to be carried out dependent upon the nature of the sample. These functions are carried out by the control computer 16 as follows. Firstly, the computer checks the tuning of the rf probe 14 by means of a pick-up coil 18 and rf monitor 19, making adjustments by means of the tuning control 20. Secondly, the matching to the rf power amplifier 13 is monitored by means of a directional coupler 21 (or directional wattmeter), which the computer responds to via a matching circuit 22, which in turn adjusts the rf probe 14 by means of a variable capacitance or inductance. The directional coupler 21 is switched out by the computer 16 when not required, via switch 23. Thirdly, the Q factor of the rf coil is monitored by a frequency-switch programme and adjusted by means of a Q-switch 24 which either changes the coil Q or alternatively alerts the computer to increase the number of measurements.

The control computer 16 may be programmed in various ways to reduce or eliminate the spurious interference described above by controlling the pulse amplitudes and phases by means of the control 10. These ways involve the use of a comparator 25 for comparing the response signals from different pulses by making appropriate changes to the phase of the receiver and detection circuitry 15, and passing the resultant signals to the remainder of the control computer 16 for further processing.

Shown diagrammatically in FIG. 2 and designated as 27 is some means, such as a conveyor belt, for transporting a succession of samples to a region adjacent the rf probe 14. The computer 16 is arranged to time the application of the excitation pulses substantially simultaneously with the arrival of a particular sample adjacent the probe. In alternative embodiments, instead of the sample being carried on a conveyor belt, it may actually be a person, and the rf probe may be in the form of a walk-through gateway or a hand-held wand.

The apparatus described above may employ simple rectangular pulses, although other pulse shapes may be employed, and each pulse described herein may be substituted by one or more suitable composite pulses. For example, the phase split pulses disclosed in WO 96/26453 (see the section entitled "Third variant of the first embodiment—phase split pulses", as well as FIGS. 2b to 2d) could be used in order to improve the excitation bandwidth. In the preferred embodiment these phase split pulses would be modified by removing the initial preparation pulse (for a disclosure of the initial preparation pulse see page 21 lines 27 to 30 of WO 96/26453).

Furthermore, although usually the radio-frequency probe would utilise a single coil for both transmission and reception of signals, any appropriate number of coils may be used, and different coils can be used for transmission and reception. Also, the apparatus would usually operate in the absence of any applied magnetic field.

First Preferred Embodiment of Pulse Sequence

In a first preferred embodiment of pulse sequence, two blocks of excitation pulses are applied to a sample, each block comprising a Steady State Free Precession (SSFP) excitation pulse sequence with no phase alternation. The resonance response signals from the two blocks are compared in appropriate fashion such that the spurious interfering signals are reduced whilst the genuine NQR signals are enhanced. Typically a difference or a weighted difference of the two response signals is determined.

In the general case, a single block may be written as $$(P\alpha_{+y}\text{-}\tau)^{acq}_n$$

where P indicates a pulse of flip angle $\alpha$ and phase +y, $\tau$ is the time between pulses and n is the number of pulse repetitions. The superscript "acq" indicates that response signals are acquired for all pulses. In one particular example, $\alpha=90°$, $y=0°$, $\tau=2$ ms and $n=2000$, although other values may be used; for example, $\alpha$ may typically take any value equal to or less than 180°. In one minor variant, a final pulse may be added after the "n" acquisitions, so that the sequence ends on a pulse rather than notionally on a delay; this is for bookkeeping purposes. This variant may be applied to all the pulse sequences disclosed herein.

In one variant, the phases of the various pulses are varied in accordance with the teachings of WO 96/26453 (see the sections entitled "second variant of the second embodiment" and "third variant of the second embodiment"), with phase varying within each individual block and also between the two blocks of the overall sequence. In that variant, the response signals from the various blocks are combined in the manner disclosed in WO 96/26453. However, that particular variant involves for each pulse a switching of the phase of the excitation pulse relative to the previous pulse. When the decay time of the spurious signals is long, that variant may not be effective in eliminating such signals since in such circumstances there can only be cancellation of the spurious signal generated by the immediately preceding pulse. Hence, in a preferred variant the phases of all of the pulses in both of the blocks are the same, and further details of this variant are now provided.

In the case where the phases of all of the pulses in both of the blocks are the same and indeed all of the pulses are identical, subtracting the response signals of the second block from those of the first block would be expected to result in complete cancellation of the genuine NQR signals as well as the spurious interfering signals. However—contrary to expectation—it has been discovered that by having a delay time $\Delta$ between excitation blocks of less than say $T_1$, so that the system is not fully relaxed prior to the application of the second excitation block, firstly the second block generates response signals of significant strength and secondly subtraction of the two response signals may—fortuitously—actually yield a non-zero residual signal, whilst still, of course, reducing spurious signals. The reason for this phenomenon is not well understood, but what is relatively clear is that an SSFP pulse sequence in NQR is in some way able to regenerate magnetisation in the z direction (that is, at right angles to the direction of the $B_1$ field generated by the excitation pulses) in a time less than 3 or 5 $T_1$.

The value of the delay time $\Delta$ between the blocks which produces the optimum residual NQR signal (once the response signal of the second block has been subtracted from that of the first block) has been the subject of considerable investigation. It appears that the prime function of the delay is to modify the magnetization between the first and second blocks, and to modify phase and/or frequency. It has been found that the important criteria in achieving this are as follows. Firstly, the value must be very much less than $T_1$; otherwise the result of the subtraction is a zero residual signal. Secondly, the value must be sufficiently large for the magnetization in the x-y plane to dephase to a significant extent. Hence the value is suitably greater than once, twice, three or five times $T_2$. Thirdly, however, the value should not be too great since this would make the total duration of the test too long. A preferred range is 1 to 5 times $T_2$, and more preferably 2 to 4 (or 5) times $T_2$. Fourthly, the value of $\Delta$ is advantageously at least the excitation pulse separation time ($\tau$), and it is preferably at least 2, 3 or 5 times the pulse separation time. Otherwise, subtracting the response signals of the second block from those of the first can result in complete cancellation of the genuine NQR signals. Fifthly and finally, a further upper limit on $\Delta$ is that it is advantageously no greater than, say, 2, 3 or 5 times $T_{2e}$, the echo decay time.

These criteria and observations concerning the delay time $\Delta$ apply equally to all embodiments described herein.

It is believed that an important further function of the delay is to shift somewhat the relative locations of the frequency peaks and troughs which would be generated by the first and second blocks, so that the peaks generated by the first block would generally coincide with the troughs generated by the second block. Introducing a delay can be viewed as introducing a variation to phase and/or frequency.

Figure 1:
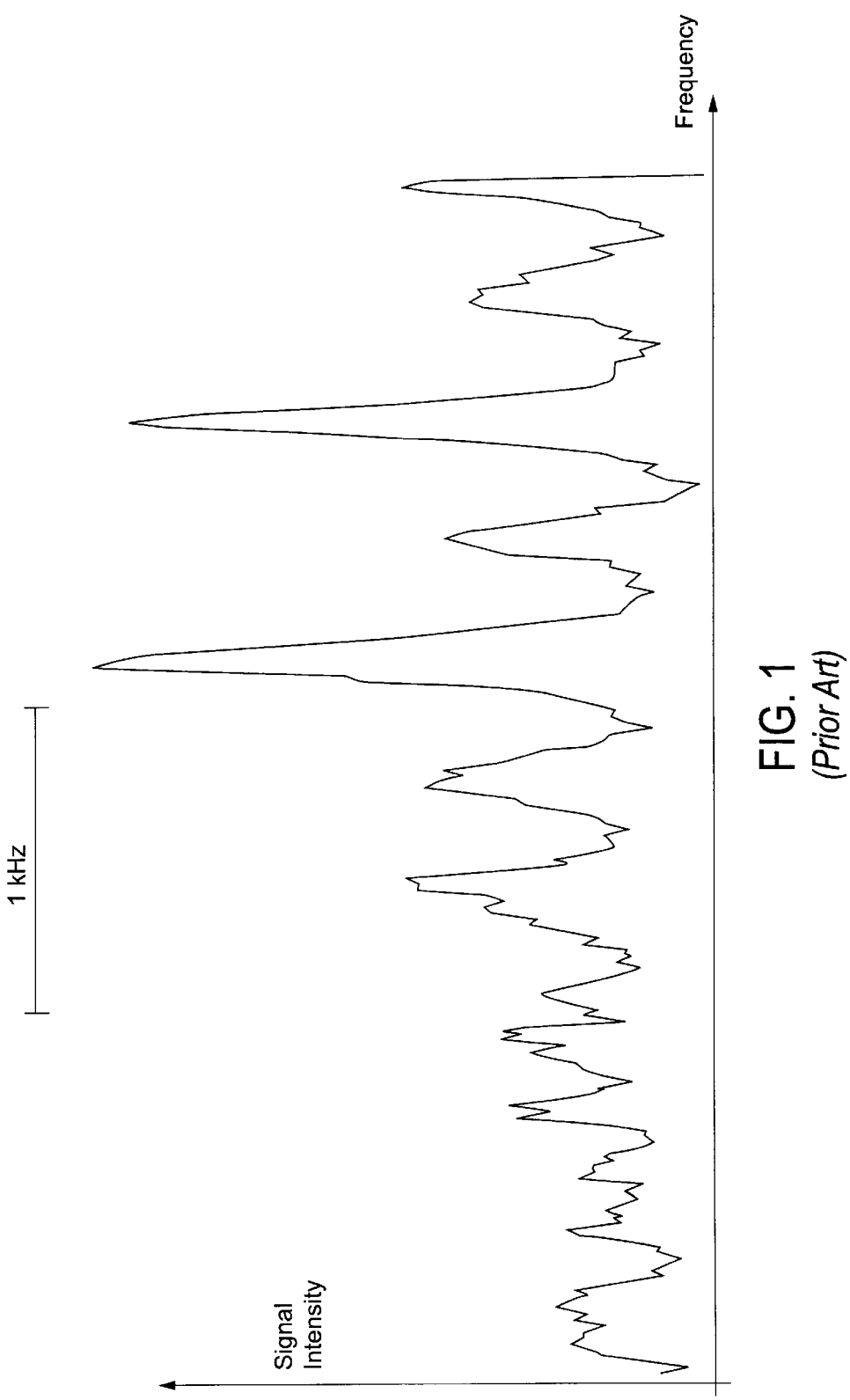
FIG. 1 shows the off-resonance response of a typical NQR substance to a multiple pulse sequence which is not $T_1$ limited.
Figure 3:
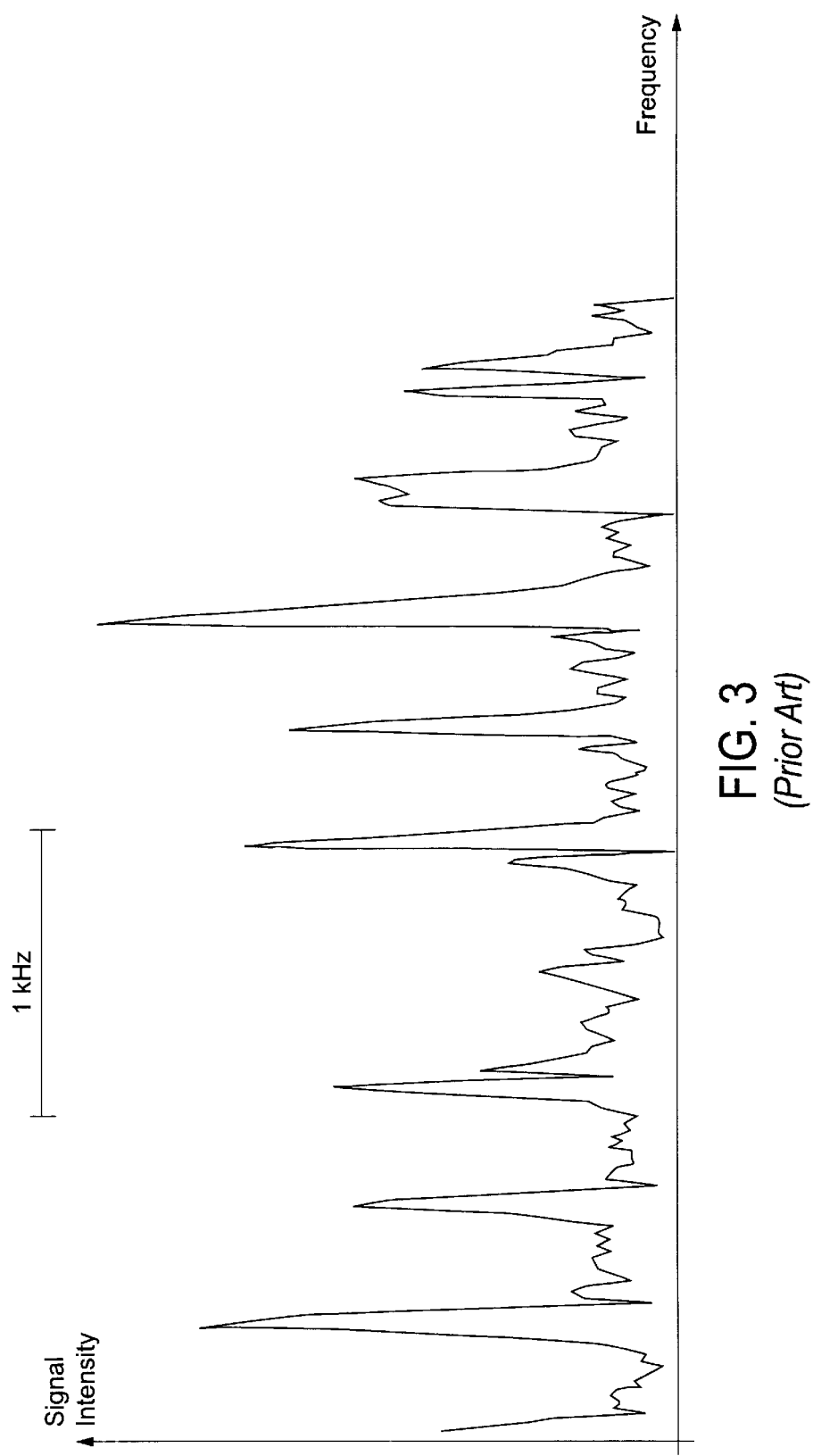
FIG. 3 shows the off-resonance response of a typical NQR substance to a first preferred embodiment of $T_1$ limited pulse sequence.

FIG. 3 shows the off-resonance response of a typical substance (such as PETN) when the pulse sequence of the preferred variant (all phases identical) of the first preferred embodiment is used. In this example, the time delay, $\Delta$, between the two blocks was roughly $3T_2$. The actual signal shown (in common with that shown in FIG. 1) is the residual signal obtained by subtracting the response signal of the second block from that of the first block. However, in contrast to the situation shown in FIG. 1 (where a time delay of greater than $T_1$ is left between the two blocks), the pulses in the pulse sequences used to produce the responses have identical phase, and hence subtracting the respective responses would be expected to give no residual signal. However, it can be seen that, unexpectedly, a useable off-resonance response is nonetheless produced.

The off-resonance response may be further improved by using the techniques of the other preferred embodiments, and especially of the fourth and/or fifth and/or sixth embodiment, as will be discussed later.

Second Preferred Embodiment of Pulse Sequence

In a second preferred embodiment of pulse sequence, both excitation blocks comprise Pulsed Spin Locking (PSL) pulse sequences. As was described in WO 96/26453 (see the first variant of the second embodiment), PSL sequences can provide efficient discrimination against many kinds of spurious response, with appropriate cycling of the phase of the individual pulses. In a typical PSL sequence, each block has its own preparation pulse, $P_1$, followed by a sequence of identical pulses, $P_2$, differing in phase typically by 90° from $P_1$. In a two-block sequence, block 1 is written in general terms as $$P_1\alpha_{+x}-\tau-(P_2\alpha_{+y}-2\tau)_m-(P_2\alpha_{+y}-2\tau)^{acq}_n$$

and block 2 is the phase-cycled version $$P_1\alpha_{-x'}-\tau-(P_2\alpha+y-2\tau)_m-(P_2\alpha_{+y}-2\tau)^{acq}_n$$

In this case the preparation pulse is followed by m pulses during which response signals are preferably not acquired (in order to allow sufficient time for the spurious interfering signals following the preparation pulse to decay, given that such signals cannot be eliminated since the pulse is of different phase), and then n pulses during which response signals are acquired. The phase $-x'$ of the preparation pulse in block 2 may be 180° different from that ($+x$) of the first block (that is $x=-x'=90°$), although other values may be used, especially if a more complete cycling of phases is carried using more than two excitation blocks. The relative phase $+y$ of the subsequent pulses would typically be zero, although again other values are possible.

In a two block sequence, the response from one block is subtracted from the other. If phase-cycling is used then the responses from blocks having preparation pulses which differ by 180° are subtracted from each other, and the resultant residual signals are added.

As described in WO 96/26453, the above sequence can produce a 33 dB rejection of spurious responses. Such a sequence can allow spurious responses generated by the $P_2$-type pulses to be cancelled.

As with the first preferred embodiment, in the second preferred embodiment, two blocks of PSL pulses are applied with a delay time $\Delta$ between the two blocks of less than $T_1$. Again, the optimum value of the delay time has been found to be about one to five times $T_2$, although other values may be used.

Values of m and n may typically be in the ranges 2 to 8 and 200 to 1000° respectively, although other values are possible. Particularly preferred values of m and n are 4 and 2000 respectively.

Figure 4:
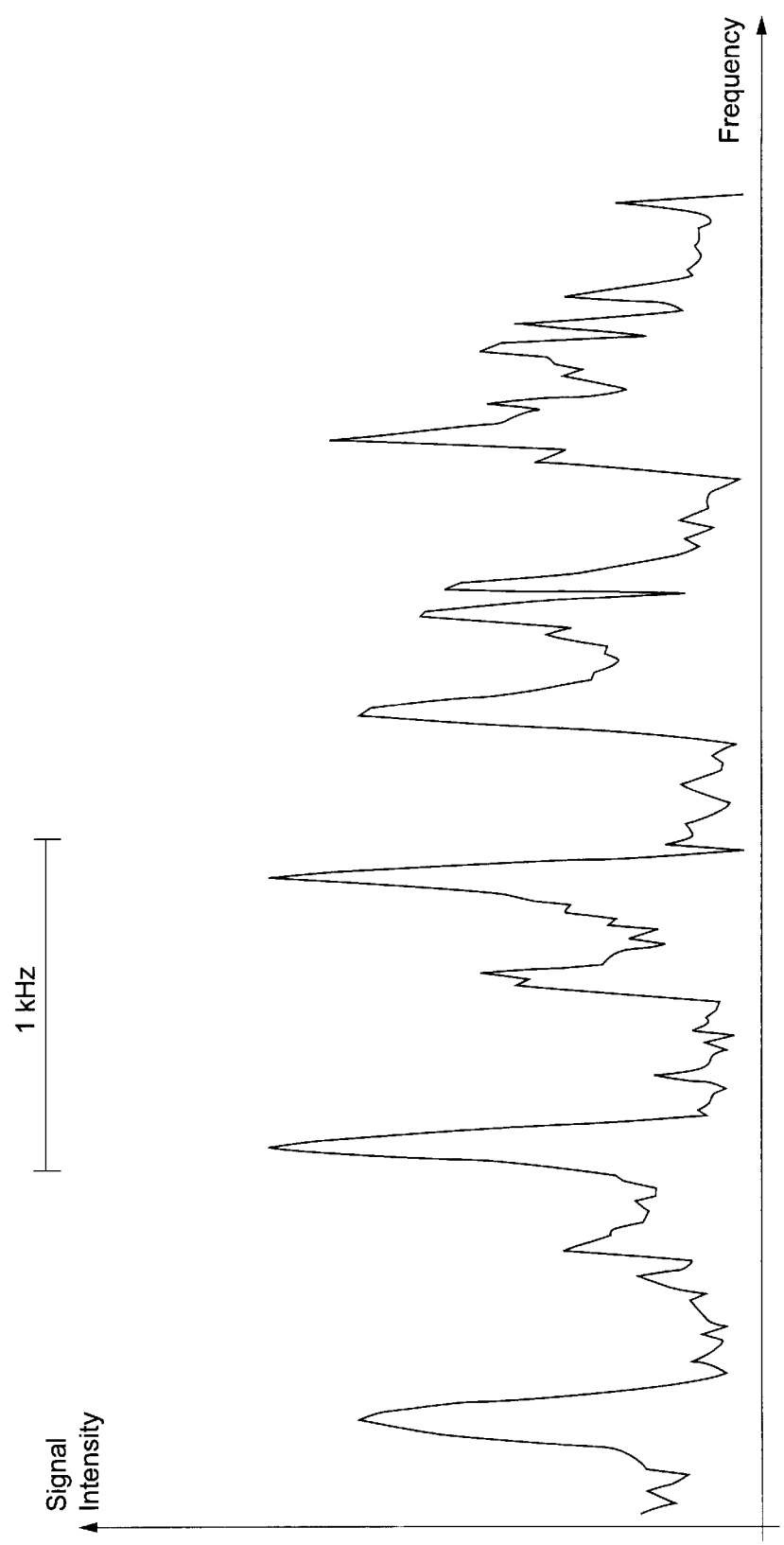
FIG. 4 is an equivalent figure for a second preferred embodiment of pulse sequence.

FIG. 4 shows the off-resonance response of a typical substance when the pulse sequence of the second preferred embodiment is used. In this example, the time delay, $\Delta$, between the two blocks was again roughly $3T_2$. The actual signal shown (in common with that shown in FIG. 1) is the residual signal obtained by subtracting the response signal of the second block from that of the first block. It can be seen that the peaks are wider and the troughs narrower than in the response for the comparable PSL blocks where the delay time between blocks is greater than $T_1$, this being the situation shown in FIG. 1. This is particularly advantageous where the precise temperature of the sample, and therefore the required excitation frequency, is not known.

It is noted that the PSL sequence described above, unlike the SSFP sequence of the first embodiment, involves a phase change between the first and second excitation blocks, so that (again unlike the SSFP sequence) a subtraction of the response signals of the second block from those of the first block yields a non-zero result, even for a $T_1$ limited sequence.

Third Preferred Embodiment of Pulse Sequence

The third preferred embodiment of pulse sequence is similar to the second, except that the delay between the preparation pulse (at least for one of the blocks, and preferably the first block) and the subsequent pulses is different. The purpose of such a variation to the PSL sequence known from WO 96/26453 is to shift somewhat the locations of the frequency peaks and troughs which would be generated by the first and second blocks, so that the peaks generated by the first block would generally coincide with the troughs generated by the second block. Introducing a variation to the pulse separation can be viewed as introducing a variation to phase and hence frequency.

Block 1 may be written as $$P_1\alpha_{+x}-\tau'-(P_2\alpha_{+y}-2\tau)_m-(P_2\alpha_{+y}-2\tau)^{acq}_n$$

and block 2 is the phase-cycled version $$P_1\alpha_{-}-\tau''-(P_2\alpha_{+y}-2\tau)_m-(P_2\alpha_{+y}-2\tau)^{acq}_n$$

In the preferred variant of the third embodiment, $\tau'$ is equal to $2\tau$, although it may have a value in the range of, say 1.5 to $2.5\tau$. Nonetheless, the value of $2\tau$ is viewed as being particularly preferable. In this preferred variant, $\tau''$ would equal $\tau$, although other values are possible.

In other preferred variants, the variation of pulse separation may take place in the second block rather than the first (that is, $\tau''$ would most preferably be equal to $2\tau$). However, since the overall signal generated by the second block is likely to be less than that generated by the first block, such a variant is less preferred. Again, both $\tau'$ and $\tau''$ may be different from the values described in relation to the second preferred embodiment.

Fourth Preferred Embodiment of Pulse Sequence

In the fourth preferred embodiment of pulse sequence, one or more so-called "refocussing" pulses are applied in the delay time $\Delta$ between the two excitation blocks. The excitation blocks may be the blocks of any of the first three preferred embodiments, in any suitable combination.

The refocussing pulse is preferably located at the maximum of the last echo generated by the first block (that is, at a time $\tau$ after the last pulse), although the pulse could be applied at other delays after the end of the first excitation block. The purpose of the refocussing pulse is to restore some or all of the magnetization in the x-y plane to the z-direction; this then restores the spin system ready for the second excitation block. Although it might be thought that in order to refocus magnetization from the x-y plane to the z-direction a $90°_{effective}$ flip angle would be most preferred, in fact a whole range of flip angles has in practice been found to function successfully. Preferred ranges of effective flip angle for the refocussing pulse are between 20° and 340° and preferably either between 30° and 60° or between 70° and 110° or between 160° and 200°. In one example the refocussing pulse has an effective flip angle of 45°. In another example the flip angle is 90°. In a further example, a 90° pulse is used at the maximum of the echo from the last pulse in the block, to put the magnetisation back into the z-direction, and then a 45° pulse is used to put the magnetisation back into the x-y plane in the opposite direction.

When using a refocussing pulse, a relatively short total delay time between the two excitation blocks may be used (perhaps equal to or (somewhat) greater than $4\tau$, $2\tau$ in this case being the pulse separation time).

The phase of the refocussing pulse has been found to be relatively unimportant in situations of practical interest, although it is preferred that the pulse be of opposite phase to the phase of the first pulse of the first block.

Figure 5:
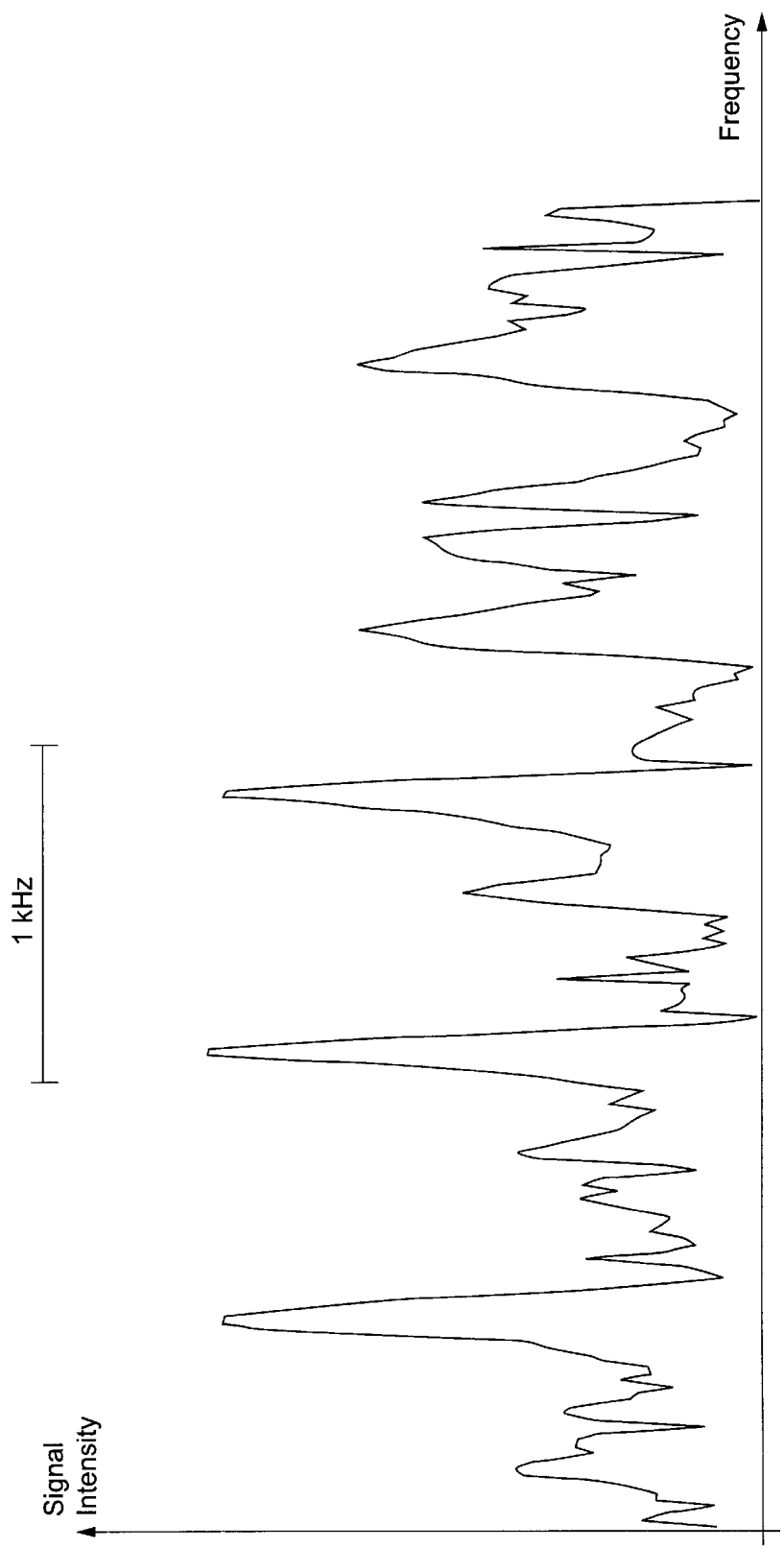
FIG. 5 is an equivalent figure for a fourth preferred embodiment of pulse sequence.

FIG. 5 shows the off-resonance response of a typical substance when two PSL blocks of the second embodiment are used, and a refocussing pulse of flip angle 45° is applied between the two blocks. The total time delay, $\Delta$, between the two blocks was again roughly $3T_2$. The actual signal shown (in common with that shown for example in FIG. 1) is the residual signal obtained by subtracting the response signal of the second block from that of the first block. It can be seen that the use of a refocussing pulse gives an improvement in the response by comparison with the response shown in FIG. 4.

Fifth Preferred Embodiment of Pulse Sequence

In a fifth preferred embodiment, one or more pulses of preferably 180° effective flip angle, termed "windmill" pulses, are applied between the two excitation blocks, with the delay between the end of the first block and the first such windmill pulse, and the delay between the first windmill pulse and any subsequent other pulses, being between preferably one and five times $T_2$, and more preferably two and four times $T_2$. The excitation blocks may be the blocks of any of the first three preferred embodiments. The purpose of at least the initial windmill pulse is to modify the phase component of the magnetization as well as to drive it back along the z-direction. The purpose of the further such pulses is to store the magnetization between the blocks. It can be seen that one function of the windmill pulses is to introduce an effective phase shift (and hence frequency shift) between the first and second blocks, so that the peaks generated by the first block would generally coincide with the troughs generated by the second block.

For example, based on a value of $3T_2$ of 40 ms, four windmill pulses may be applied with a delay of 40 ms between each, giving a total delay time between the two excitation blocks of about 200 ms. It is important that this total time be considerably less than $T_1$.

The number of windmill pulses has been found not to be critical. Better results are obtained with two or more such pulses than with just one such pulse, although five or more pulses do not make an appreciable difference. Nonetheless, larger numbers of pulses may be useful if it is desired to store the magnetization any longer, for example, in case it were desired to switch frequency between the first and second blocks.

The flip angle of the windmill pulses is preferably close to 180° (so as to achieve the necessary phase change for the second excitation block), and may be typically in the range 150 to 210° although it may be even as low as 30 to 90°. The phase of the pulses has been found to be relatively unimportant, although "+x" is preferred.

Figure 6:
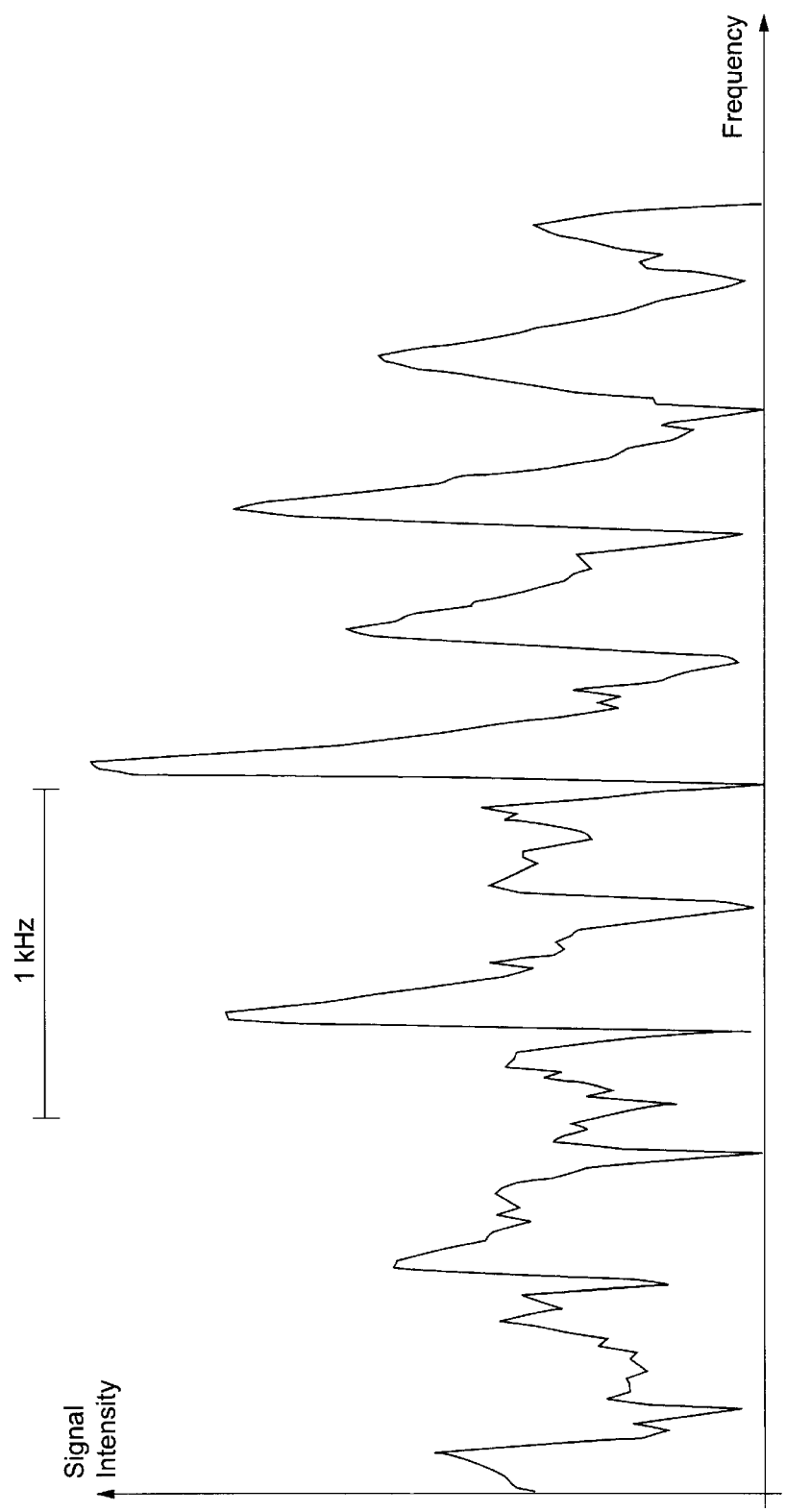
FIGS. 6 to 9 are equivalent figures for a fifth preferred embodiment of pulse sequence under a variety of different conditions.
Figure 7:
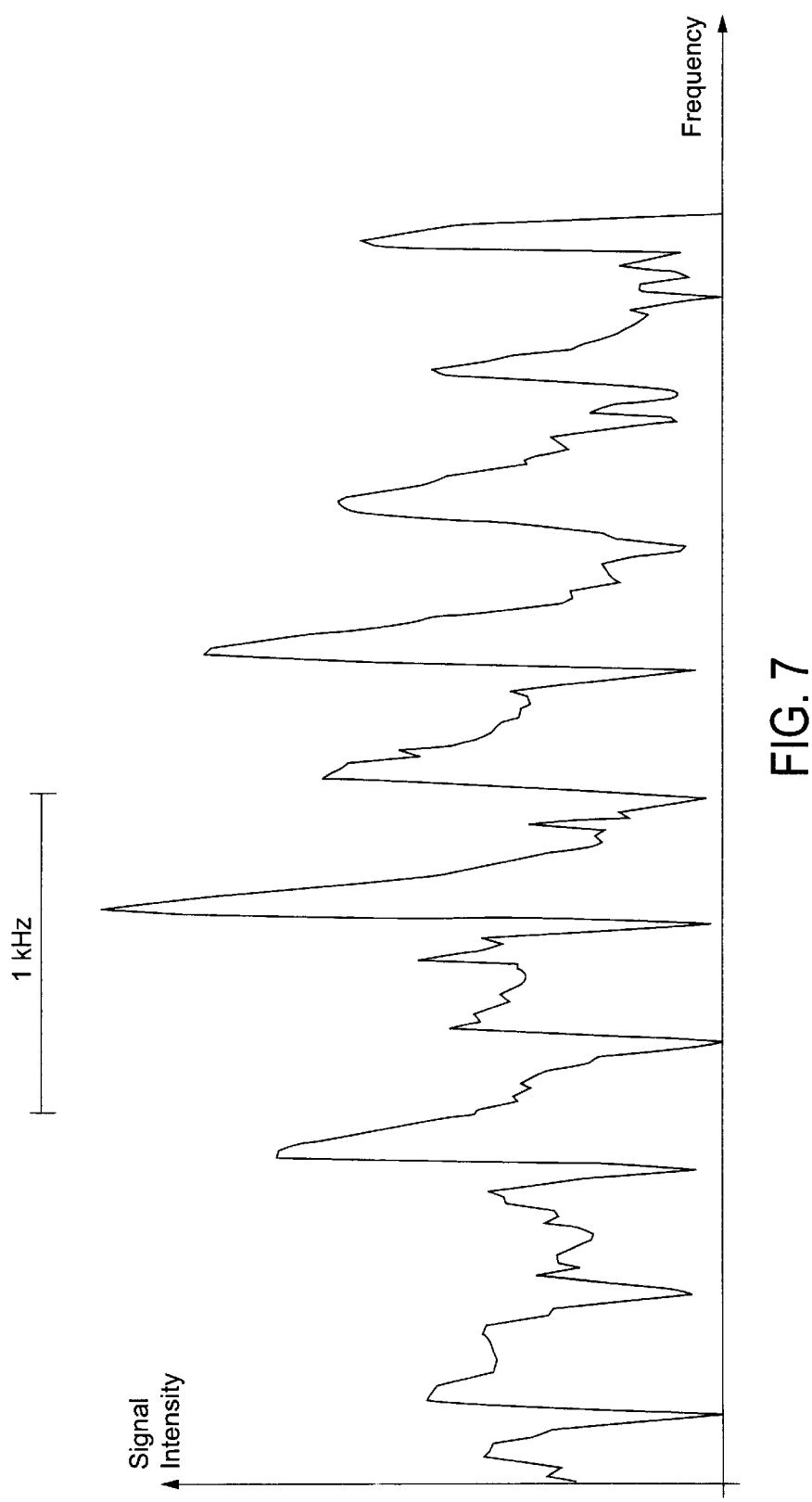

FIG. 6 shows the off-resonance response of a typical substance when two PSL blocks of the second preferred embodiment are used and a single windmill pulse applied between the blocks. FIG. 7 shows the off-resonance response of a typical substance when two PSL blocks of the third preferred embodiment are used and a windmill pulse applied between the blocks. It can be seen that in both cases there is a significant improvement in the response, with the improvement being better in the case of FIG. 7.

Figure 8:
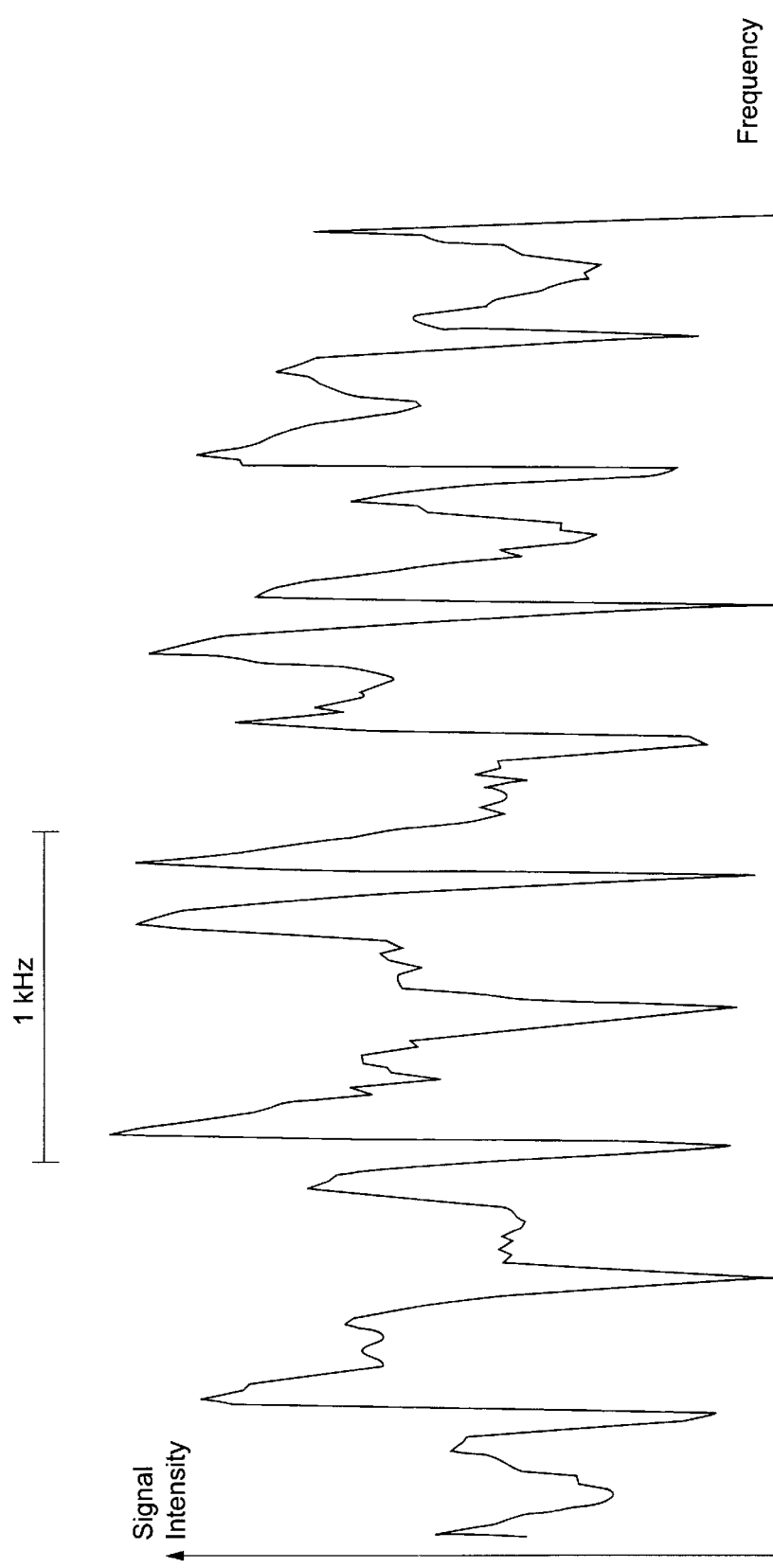
Figure 9:
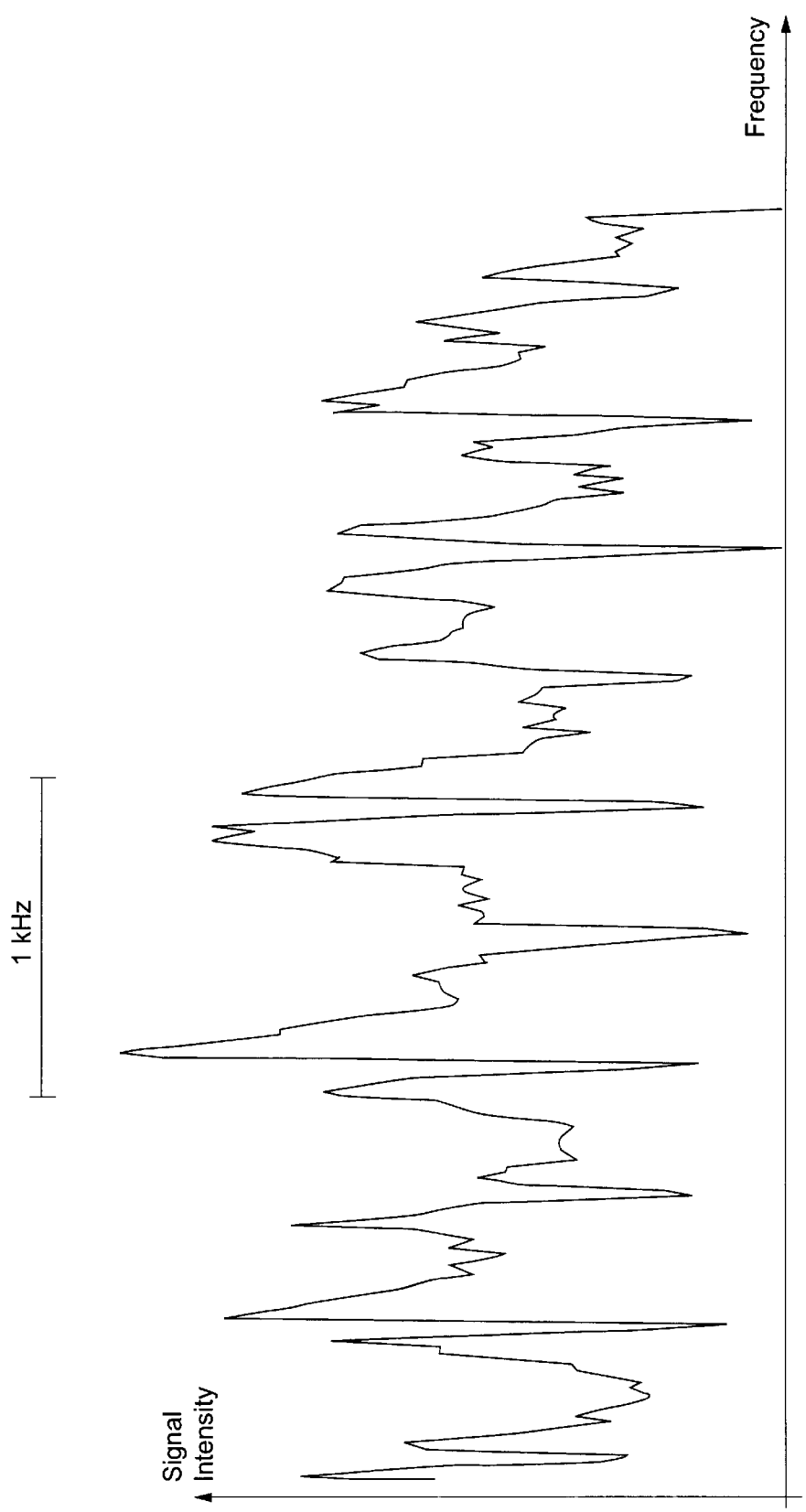

FIGS. 8 and 9 show the off-resonance response of a typical substance when two SSFP blocks of the first preferred embodiment are used and windmill pulses applied between the blocks. In the case of FIG. 8 a single windmill pulse was used, while in the case of FIG. 9 four windmill pulses were used. It can be seen that in both cases there is a significant improvement in the response.

Figure 10:
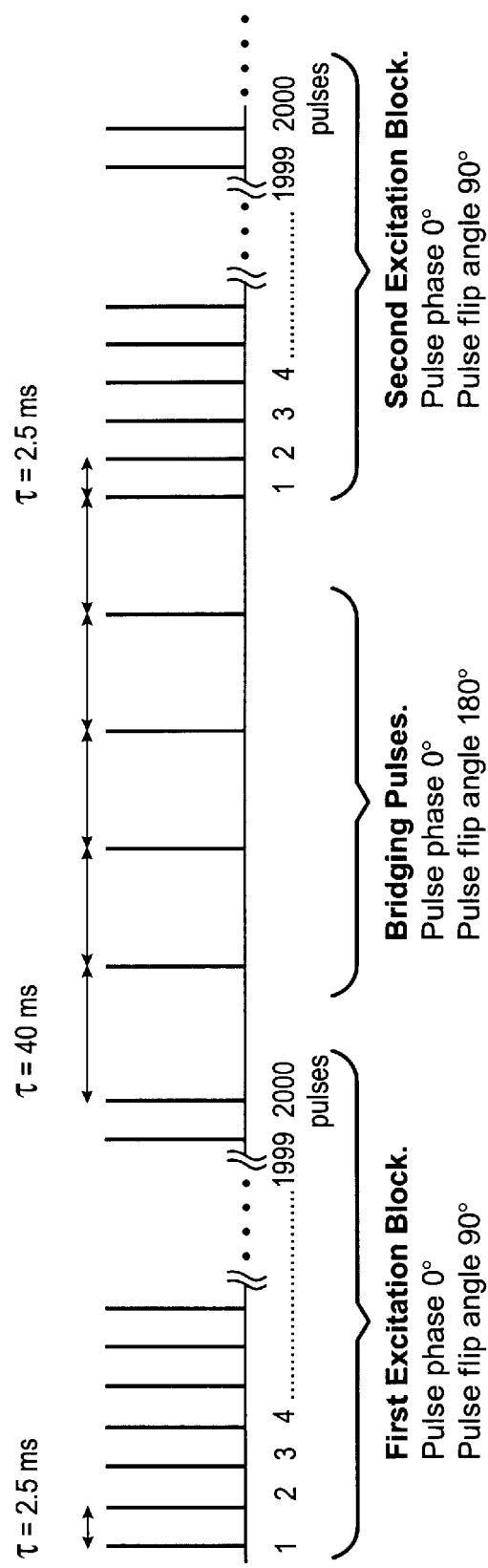
FIG. 10 illustrates the pulse sequence employed in the generation of the plot of FIG. 9.

The overall pulse sequence employed in the generation of the plot of FIG. 9 is illustrated in FIG. 10. This figure shows the number, spacing, phase and flip angle of the various pulses in the first, second and bridging blocks of pulses.

Sixth Preferred Embodiment of Pulse Sequence

According to a sixth preferred embodiment, a number of so-called "saturation pulses" are applied in the delay time between the two excitation blocks. The excitation blocks may be any of the blocks of any of the first three embodiments, in any combination. Saturation pulses scramble the NQR spins so that the net energy difference in the NQR system is zero, with the result that no NQR signal can be detected.

In order to achieve saturation, two or more 90° effective pulses may be employed, typically with a variable delay between the pulses. Typically, at least two, three, five or ten such pulses might be applied. For example, eleven 90° effective pulses might be applied, with a short but variable delay (for example, between 100 µs and 50 ms) between each pulse.

The result of applying the saturation pulses is that substantially no signal is detected from the second excitation block; however, spurious signals are not substantially affected by the saturation pulses (since they are not NQR signals). Therefore, in the present embodiment, comparing the responses from the respect blocks will result in a reduction in the spurious signals while leaving the NQR signal from the first block substantially unaltered.

Seventh Preferred Embodiment of Pulse Sequence

According to a seventh preferred embodiment, two pairs of excitation blocks (or sub-blocks) are applied, with the pairs interleaved such that one sub-block of each pair acts as the bridging element for the other pair. Such a sequence may be written in general terms as

SUB-BLOCK 1–Δ–SUB-BLOCK 2–Δ–SUB-BLOCK 3–Δ–SUB-BLOCK 4

Sub-blocks 1 and 3 make up one pair of identical blocks of pulses, and sub-blocks 2 and 4 another identical pair (which may or may not be the same as the first pair). The sub-blocks may be the blocks of any of the first three preferred embodiments, in any appropriate combination.

The response from sub-block 1 is compared to that from sub-block 3, and the response from sub-block 2 is compared to that from sub-block 4, and the compared responses are then combined. Such sequences have the advantage that the second and third sub-blocks act as bridging elements, and are also used to acquire signal responses.

Another way of viewing the seventh embodiment is that sub-blocks 1 and 2 as defined immediately above form a first main block and that sub-blocks 3 and 4 form a second main block, there being a delay between the first and second main blocks which may include bridging pulses if required. Accordingly, the first and second main blocks and the delay therebetween effectively form the basic sequence of

FIRST BLOCK–BRIDGING ELEMENT–SECOND BLOCK

Preferably, one pair of sub-blocks uses a different pulse sequence from the other pair of sub-blocks, so that the resonance response profile obtained from the two pairs of sub-blocks is different. For example, the delay between the pulses in one pair of sub-blocks may be different from the delay between the pulses in the other pair of sub-blocks, or the lengths of the pulses may be different, or the phases may be different.

Advantageously, by judicious choice of elements in the sub-blocks the peaks in one response profile are arranged to coincide as far as possible with the troughs of the other response profile. Thus, combining the respective resonance response profiles results in an improved overall off-resonance response.

Other bridging pulses, such as one or more refocussing pulses of the fourth preferred embodiment and/or one or more windmill pulses of the fifth preferred embodiment and/or the saturation pulses of the sixth preferred embodiment, may be applied between the excitation sub-blocks of a pair. Preferably, any such pulses are applied between sub-block 2 and sub-block 3, so that they act as bridging pulses for both pairs of excitation sub-blocks, although they may alternatively or additionally be applied between sub-blocks 1 and 2, and sub-blocks 3 and 4.

In a particularly preferred example of the seventh preferred embodiment, the following pulse sequence is used.

$$(P_y - \tau_1 - P_y)_n - \Delta - (P_y - \tau_2 - P_y)_n - \Delta -$$
$$(1) \qquad\qquad (2)$$

$$(P_x - \delta -)_m - (P_y - \tau_1 - P_y)_n - \Delta - (P_y - \tau_2 - P_y)_n$$
$$(3) \qquad\qquad\qquad (4)$$

This pulse sequence consists of one pair of sub-blocks (1) and (3) having a delay $\tau_1$ between the pulses interleaved with another pair of sub-blocks (2) and (4) having a delay $\tau_2$ between the pulses, where $\tau_1 \neq \tau_2$. A number m of saturation pulses are applied between sub-blocks 2 and 3. The delays Δ between the sub-blocks may or may not be the same.

In order to increase off-resonance performance, the pulse repetition rate may differ between the two pairs of sub-blocks. This may be achieved either by setting $\tau_1 \neq \tau_2$ (as just described) or by varying the pulse length, or both.

There is a variable delay δ between each saturation pulse, in order to suppress echoes.

Figure 11:
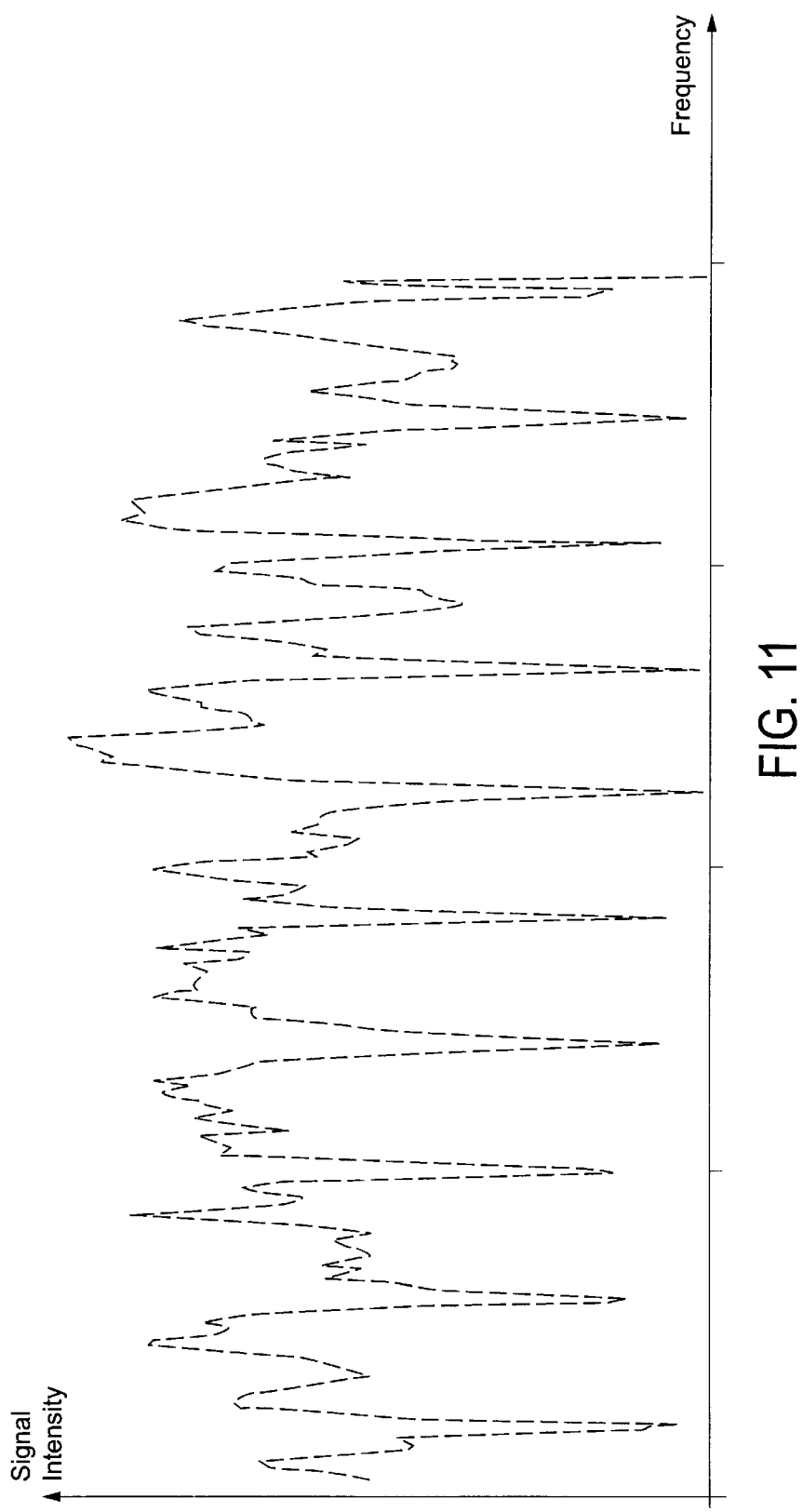
FIG. 11 is a figure equivalent to FIG. 3 using the sixth and seventh preferred embodiment of pulse sequence together.

FIG. 11 shows the off-resonance response of a typical substance when the above excitation sequence is used. It can be seen that there is a significant improvement in the response over FIG. 1.

Figure 12:
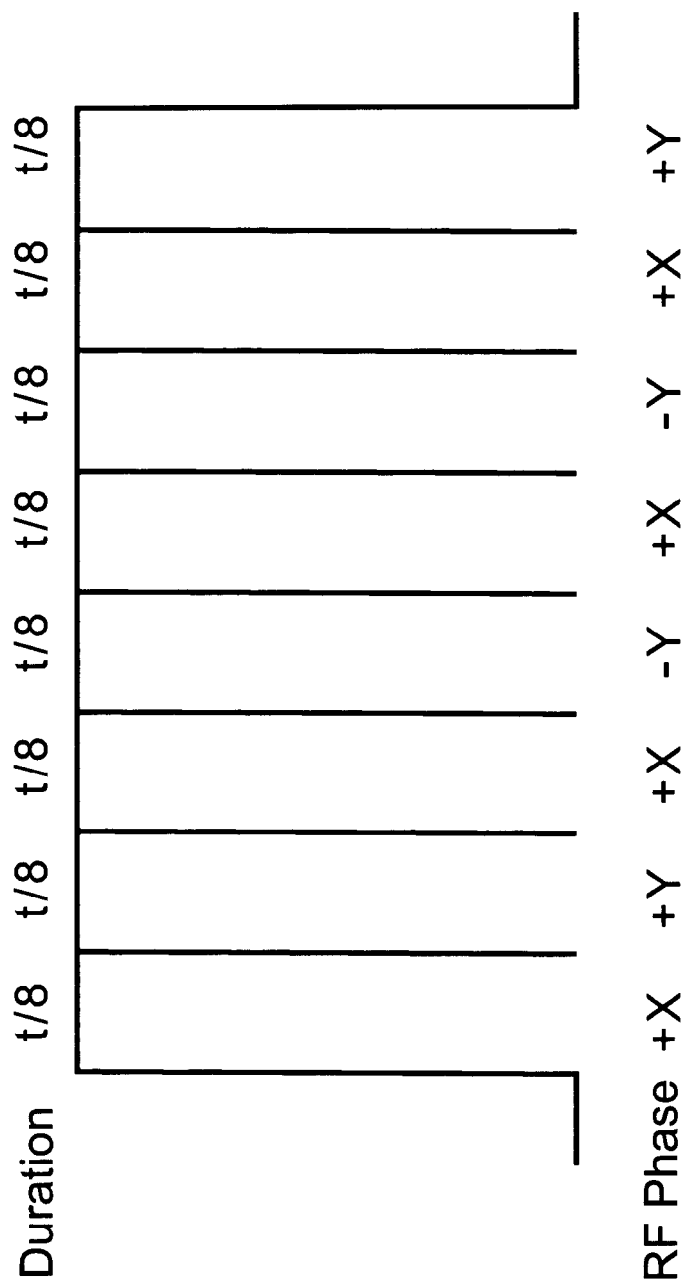
FIG. 12 illustrates a phase split pulse.

In the example shown in FIG. 11, each pulse is a phase split pulse similar to those described above, and as shown in FIG. 12. Each pulse has a total length of 400 µs, a $B_1$ field of 0.1 mT, Δ=40 ms and δ is varied randomly between 100 µs and 50 ms in order to suppress echoes. $\tau_1$ is 2.6 ms and $\tau_2$ is 3.9 ms. This has the effect of overlapping the responses of two sequences having differing repetition rates.

Taking as a whole the results shown in FIGS. 3 to 9 and 11, it can be seen that (dependent perhaps upon the particular substance being examined): a) short delays between blocks (<<$T_1$) give better performance (defined in this instance as a weaker offset dependence) than long delays (~$T_1$ and above); b) the addition of a pulse of a given length and a given phase between the blocks improves performance; c) an 180° "effective" pulse with a phase of +x gives best results; d) these pulses can be used singly or in sets of two or more in combination with delays of various lengths from τ to something less than $T_1$, without any great penalty in intensity drop-off (effectively allowing magnetization to be "stored" between blocks); and, finally, e) SSFP gives a better performance than PSL in all circumstances except the use of a simple, short delay. With the best results, any remaining troughs in the frequency characteristic are unlikely to be of practical consequence.

In these experiments, when using a single pair of blocks, SSFP blocks with four windmill pulses were found to give the best results, while using two pairs of sub-blocks in the manner described in the seventh preferred embodiment gave the best overall results.

Any of the preferred embodiments may be used in combination with any of the other preferred embodiments. For example the windmill pulses may also be used in combination with the refocusing pulse of the fourth preferred embodiment. Furthermore, a PSL first block may be combined with a SSFP second block, and vice versa.

In any of the preferred embodiments, the phases of the pulses may be cycled as taught in WO 96/26453.

In summary, the present technique may be represented in general terms as

FIRST BLOCK–BRIDGING ELEMENT–SECOND BLOCK

The first block may comprise any of the following pulse sequences $$(P\alpha_{+y}-\tau)^{acq}_n$$

$$P_1\alpha_{+x}-\tau-(P_2\alpha_{+y}-2\tau)_m-(P_2\alpha+y-2\tau)^{acq}_n$$

$$P_1\alpha_{+x}-\tau'-(P_2\alpha_{+y}-2\tau)_m-(P_2\alpha+y-2\tau)^{acq}_n$$

The bridging element may comprise any of the following elements (in any number)

$$\Delta$$

$$\Delta-P\theta_\phi$$

$$\Delta-(P180_\phi-\Delta)_n$$

$$\Delta-(P90_\phi-\delta)_n$$

or any combination thereof, where $\Delta$ and $\delta$ are delays ($\delta$ being shorter than, preferably much shorter than, $\Delta$), $\theta$ is an arbitrary flip angle and $\phi$ is arbitrary phase.

The second block may comprise any of the following pulse sequences $$(P\alpha_{+y}-\tau)^{acq}_n$$

$$P_1\alpha_{+x}-\tau-(P_2\alpha_{+y}-2\tau)_m-(P_2\alpha_{+y}-2\tau)^{acq}_n$$

$$P_1\alpha_{-x}-\tau''-(P_2\alpha_{+y}-2\tau)_m-(P_2\alpha_{+y}-2\tau)^{acq}_n$$

The techniques described above give spurious signal suppression and allow excitation to be used off-resonance, and are particularly advantageous in the detection of substances with low NQR frequencies and high values of $T_1$. The techniques provide the additional advantage of requiring a short detection time. The techniques are therefore well suited to detection in non-laboratory environments such as in airports and minefields, and to the detection of substances such as PETN, TNT and $KNO_3$.

It will be understood that the present invention has been described above purely by way of example, and modifications of detail can be made within the scope of the invention.

Each feature disclosed in the description, and (where appropriate) the claims and drawings may be provided independently or in any appropriate combination.

Any reference numerals appearing in the claims are by way of illustration only and shall have no limiting effect on the scope of the claims.

What is claimed is:

1. A method of Nuclear Quadrupole Resonance testing a sample containing quadrupolar nuclei exhibiting a given value of spin-lattice relaxation time, T1, the method comprising:
    applying a first excitation block, the first excitation block comprising a plurality of pulses which are such as to generate multiple echo signals;
    accumulating signals generated by the first excitation block to yield a first response signal;
    applying a second excitation block, the second excitation block comprising a plurality of pulses which are such as to generate multiple echo signals, at least the majority of the pulses being substantially the same as the corresponding pulses in said first excitation block;
    accumulating signals generated by the second excitation block to yield a second response signal; and
    comparing the first and second response signals;
    wherein the time between the end of the first excitation block and the beginning of the second excitation block is less than the T1 value of the nuclei.

2. A method according to claim 1, wherein the quadrupolar nuclei exhibit a given value of spin-spin relaxation time, T2, and the time between the end of the first excitation block and the beginning of the second excitation block is greater than the T2 value.

3. A method according to claim 1, wherein the first excitation block and the second excitation block are both such as to produce a steady state condition.

4. A method according to claim 1, wherein said first and second excitation blocks both comprise a Steady State Free Precession pulse sequence.

5. A method according to claim 1, wherein said first and second excitation blocks both comprise a Pulsed Spin Locking pulse sequence.

6. A method according to claim 1, wherein the first and second excitation blocks and the delay time therebetween are arranged such that, if the resonance frequency of the nuclei were varied over a given range, the first and second blocks would generate response signals whose variation with frequency over the given range would in combination be less than for the response signals from separately either the first or second block.

7. A method according to claim 1, wherein the sample may give rise to spurious signals which interfere with response signals from the quadrupolar nuclei, the spurious signals having a given decay time, and wherein a time between two adjacent pulses in an excitation block is less than the decay time of the spurious signals.

8. A method according to claim 1, wherein the time between the first and second pulse in the first excitation block is different from the time between the first and second pulse in the second excitation block.

9. A method according to claim 1, wherein each excitation block comprises an initial preparation pulse followed by at least one pulse of different phase from the preparation pulse.

10. A method according to claim 1, wherein at least one of the pulses in an excitation block is a phase split pulse.

11. A method according to claim 1, wherein an excitation pulse not forming part of said first and second excitation blocks is applied during the time between the end of the first excitation block and the beginning of the second excitation block.

12. A method of Nuclear Quadrupole Resonance testing a sample containing quadrupolar nuclei, the quadrupolar nuclei having an equilibrium magnetization state in the absence of applied excitation, the method comprising:
    applying a first excitation block, the first excitation block comprising a plurality of pulses which are such as to generate multiple echo signals;
    accumulating signals generated by the first excitation block to yield a first response signal;
    applying a second excitation block, the second excitation block comprising a plurality of pulses which are such as to generate multiple echo signals, at least the majority of the pulses being substantially the same as the corresponding pulses in said first excitation block;
    accumulating signals generated by the second excitation block to yield a second response signal; and
    comparing the first and second response signals;
    wherein the magnetization of the quadrupolar nuclei does not recover to its equilibrium state prior to the application of the second excitation block.

13. A method of Nuclear Quadrupole Resonance testing a sample containing quadrupolar nuclei, the method comprising:
  applying a first excitation block, the first excitation block comprising a plurality of pulses which are such as to generate multiple echo signals;
  accumulating signals generated by the first excitation block to yield a first response signal;
  applying a second excitation block, the second excitation block comprising a plurality of pulses which are such as to generate multiple echo signals;
  accumulating signals generated by the second excitation block to yield a second response signal; and
  determining a difference between the first and second response signals;
  wherein an excitation pulse not forming part of said first and second excitation blocks is applied between said first and second excitation blocks.

14. A method according to claim 13, wherein said excitation pulse not forming part of said first and second excitation blocks is applied at a time substantially coincident with an echo generated by the first excitation block.

15. A method according to claim 13, wherein said excitation pulse not forming part of said first and second excitation blocks is a refocusing pulse.

16. A method according to claim 13, wherein said excitation pulse not forming part of said first and second excitation blocks is applied at a time after the last excitation pulse in the first block, which time is greater than a time between pulses in the first excitation block.

17. A method according to claim 13, wherein the quadrupolar nuclei exhibit a given value of spin-spin relaxation time, T2, and said excitation pulse not forming part of said first and second excitation blocks is applied at a time greater than T2 from the end of the first excitation block.

18. A method according to claim 13, wherein said excitation pulse not forming part of said first and second excitation blocks is applied at a time adjacent the centre of the time between the two excitation blocks.

19. A method according to claim 13, wherein said excitation pulse not forming part of said first and second excitation blocks has an effective flip angle of greater than 150°.

20. A method according to claim 13, wherein a plurality of excitation pulses not forming part of said first and second excitation blocks are applied between said first and second excitation blocks.

21. A method according to claim 13, wherein a plurality of excitation pulses not forming part of said first and second excitation blocks are applied between said first and second excitation blocks, said excitation pulses being such as to provide saturation.

22. A method according to claim 13, wherein an excitation block not forming part of said first and second excitation blocks is applied in the time between said first and second excitation blocks.

23. A method according to claim 13, wherein the quadrupolar nuclei exhibit a given value of spin-latice relaxation time, T1, and the time between the end of the first excitation block and the beginning of the second excitation block is less than the T1 value of the nuclei.

24. A method of Nuclear Quadrupole Resonance testing a sample containing quadrupolar nuclei, the method comprising:
  applying a first excitation block, the first excitation block comprising a plurality of pulses which are such as to generate multiple echo signals;
  accumulating signals generated by the first excitation block to yield a first response signal;
  a plurality applying a second excitation block, the second excitation block comprising a plurality of pulses which are such as to generate multiple echo signals;
  accumulating signals generated by the second excitation block to yield a second response signal;
  applying a third excitation block, the third excitation block comprising a plurality of pulses which are such as to generate multiple echo signals;
  accumulating signals generated by the third excitation block to yield a third response signal;
  applying a fourth excitation block, the fourth excitation block comprising a plurality of pulses which are such as to generate multiple echo signals;
  accumulating signals generated by the fourth excitation block to yield a fourth response signal;
  comparing the first and third response signals;
  comparing the second and fourth response signals; and
  determining a sum of the comparison between the first and third response signals and the comparison between the second and fourth response signals.

25. Apparatus for Nuclear Quadrupole Resonance testing a sample containing quadrupolar nuclei exhibiting a given value of spin-lattice relaxation time, T1, the apparatus comprising:
  means for applying a first excitation block, the first excitation block comprising a plurality of pulses which are such as to generate multiple echo signals;
  means for accumulating signals generated by the first excitation block to yield a first response signal;
  means for applying a second excitation block, the second excitation block comprising a plurality of pulses which are such as to generate multiple echo signals, at least the majority of the pulses being substantially the same as the corresponding pulses in said first excitation block;
  means for accumulating signals generated by the second excitation block to yield a second response signal; and
  means for comparing the first and second response signals;
  wherein the time between the end of the first excitation block and the beginning of the second excitation block is less than the T1 value of the nuclei.

26. Apparatus as claimed in claim 25 wherein the time between the end of the first excitation block and the beginning of the second excitation block is greater than the T2 value of the nuclei.

27. Apparatus as claimed in claimed in claim 25 wherein the first and second excitation blocks and the delay time therebetween are arranged such that, if the resonance frequency of the nuclei were varied over a given range, the first and second blocks would generate response signals whose variation with frequency over the given range would in combination be less for the response signals from separately either the first or second block.

28. Apparatus as claimed in claim 25, wherein the time between the first and second pulse in the first excitation block is different from the time between the first and second pulse in the second excitation block.

29. Apparatus as claimed in claim 25, wherein each excitation block comprises an initial preparation pulse followed by at least one pulse of different phase from the preparation pulse.

30. Apparatus as claimed in claim 25, wherein an excitation pulse not forming part of said first and second excitation blocks is applied during the time between the end of the first excitation block and the beginning of the second excitation block.

31. Apparatus for Nuclear Quadrupole Resonance testing a sample containing quadrupolar nuclei, the quadrupolar nuclei having an equilibrium magnetization state in the absence of applied excitation, the apparatus comprising:

means for applying a first excitation block, the first excitation block comprising a plurality of pulses which are such as to generate multiple echo signals;

means for accumulating signals generated by the first excitation block to yield a first response signal;

means for applying a second excitation block, the second excitation block comprising a plurality of pulses which are such as to generate multiple echo signals, at least the majority of the pulses being substantially the same as the corresponding pulses in said first excitation block;

means for accumulating signals generated by the second excitation block to yield a second response signal; and means for comparing the first and second response signals;

wherein the first and second excitation blocks and any further excitation are arranged such that the magnetization of the quadrupolar nuclei does not recover to its equilibrium state prior to the application of the second excitation block.

32. Apparatus for Nuclear Quadrupole Resonance testing a sample containing quadrupolar nuclei, the apparatus comprising:

means for applying a first excitation block, the first excitation block comprising a plurality of pulses which are such as to generate multiple echo signals;

means for accumulating signals generated by the first excitation block to yield a first response signal;

means for applying a second excitation block, the second excitation block comprising a plurality of pulses which are such as to generate multiple echo signals;

means for accumulating signals generated by the second excitation block to yield a second response signal; and means for comparing the first and second response signals;

wherein the apparatus is arranged to apply an excitation pulse not forming part of said first and second excitation blocks between said first and second excitation blocks.

33. Apparatus for Nuclear Quadrupole Resonance testing a sample containing quadrupolar nuclei, the apparatus comprising:

means for applying a first excitation block, the first excitation block comprising a plurality of pulses which are such as to generate multiple echo signals;

means for accumulating signals generated by the first excitation block to yield a first response signal;

means for applying a second excitation block, the second excitation block comprising a plurality of pulses which are such as to generate multiple echo signals;

means for accumulating signals generated by the second excitation block to yield a second response signal;

means for applying a third excitation block, the third excitation block comprising a plurality of pulses which are such as to generate multiple echo signals;

means for accumulating echo signals generated by the third excitation block to yield a third response signal;

means for applying a fourth excitation block, the fourth excitation block comprising a plurality of pulses which are such as to generate multiple echo signals;

means for accumulating echo signals generated by the fourth excitation block to yield a fourth response signal;

means for determining a difference between the first and third response signals;

means for determining a difference between the second and fourth response signals; and means for determining a sum of the difference between the first and third response signals and the difference between the second and fourth response signals.

* * * * *